United States Patent [19]

Sloane

[11] Patent Number: 4,475,915
[45] Date of Patent: Oct. 9, 1984

[54] HOLDER FOR A SYRINGE AND AN AMPOULE

[76] Inventor: Glenn L. Sloane, 8825 Colbath, Panorama City, Calif. 91402

[21] Appl. No.: 541,485

[22] Filed: Oct. 13, 1983

Related U.S. Application Data

[63] Continuation of Ser. No. 376,009, May 7, 1982, abandoned.

[51] Int. Cl.³ .............................................. B65B 3/32
[52] U.S. Cl. ...................................... 604/414; 141/27
[58] Field of Search .............. 604/187, 208, 403, 411, 604/414; 141/18, 24, 27

[56] References Cited

U.S. PATENT DOCUMENTS

| | | | |
|---|---|---|---|
| 2,586,581 | 2/1952 | Tschischeck | 604/111 |
| 2,677,372 | 5/1974 | Barnish, Jr. | 604/414 |
| 3,853,158 | 12/1974 | Whitty | 604/414 |
| 3,874,380 | 4/1975 | Baum | 604/414 |
| 4,178,071 | 12/1979 | Asbell | 604/187 |
| 4,252,159 | 2/1981 | Maki | 604/208 |

Primary Examiner—John D. Yasko
Attorney, Agent, or Firm—Donald D. Mon; David O'Reilly

[57] ABSTRACT

A holder for holding a syringe and an ampoule to facilitate the transfer of liquid from the ampoule to the syringe. The holder has a body with a trough-like section to receive the ampoule, and a wall member on the body adjacent to the trough-like section which is adapted to be abutted by an ampoule resting in the trough-like section. There is an aperture through the wall member to receive and support a portion of the syringe with its needle projecting into the trough-like section where it will puncture the ampoule. A rest member is spaced from the wall member and it has an aperture to receive and support the syringe. At least a portion of the boundary of each of the apertures serves to align the syringe so its needle is directed accurately toward an ampoule that rests in the trough-like section. If desired, a magnifier can extend at least part of the distance between the rest member and the wall member to improve the readability of the numbers on the syringe.

12 Claims, 12 Drawing Figures

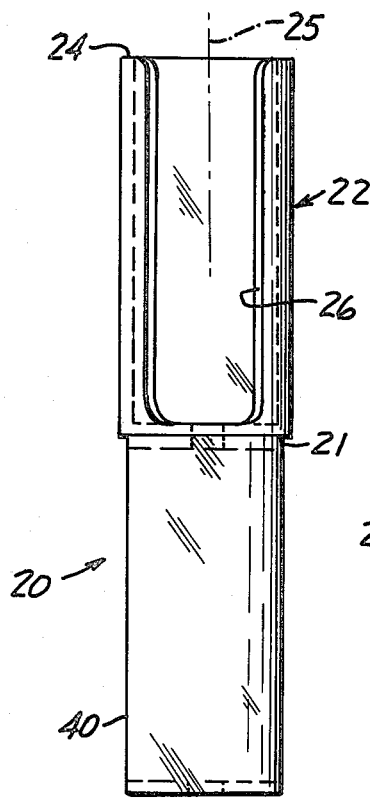
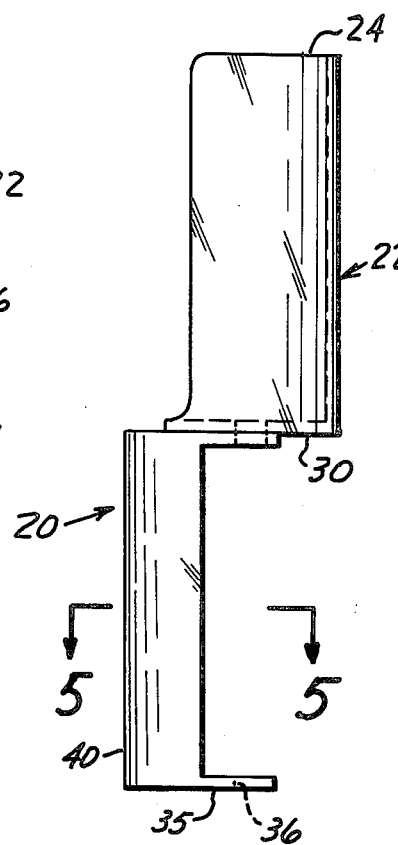
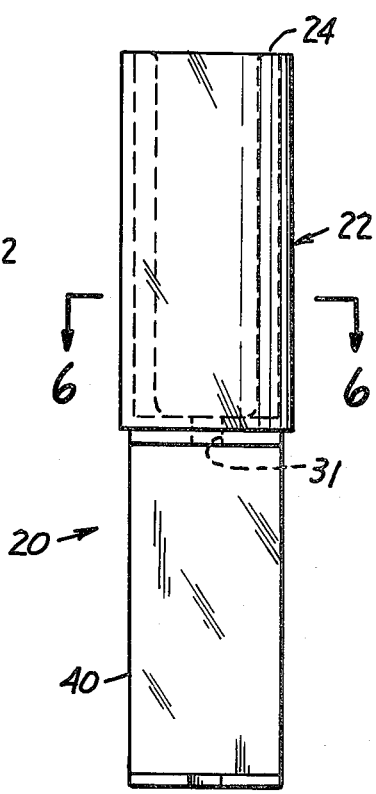
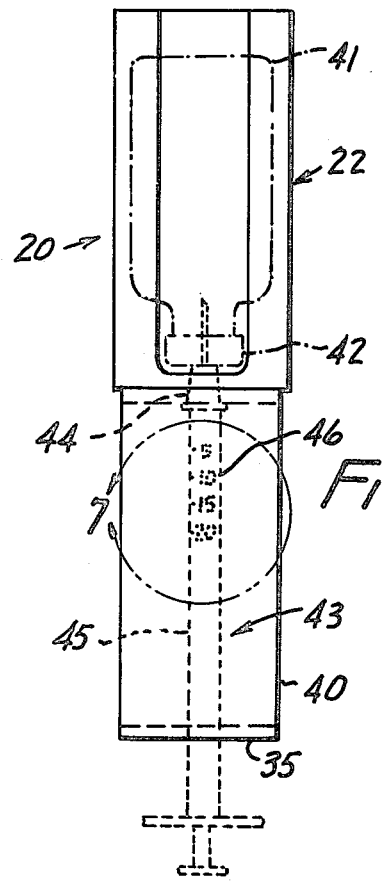
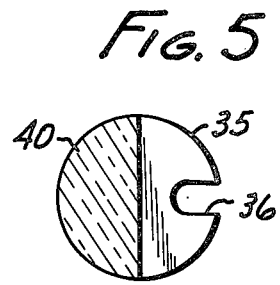
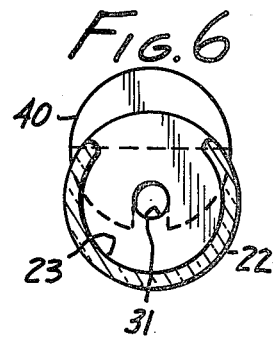
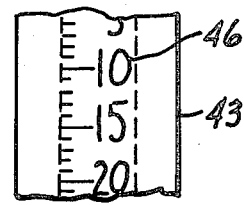

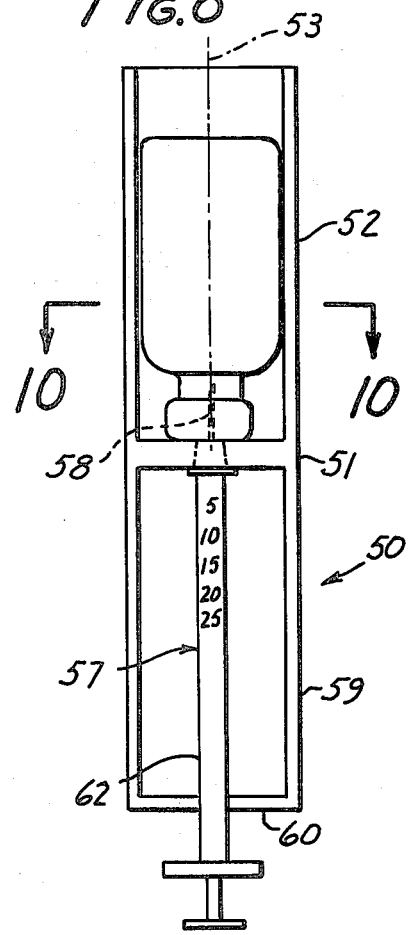
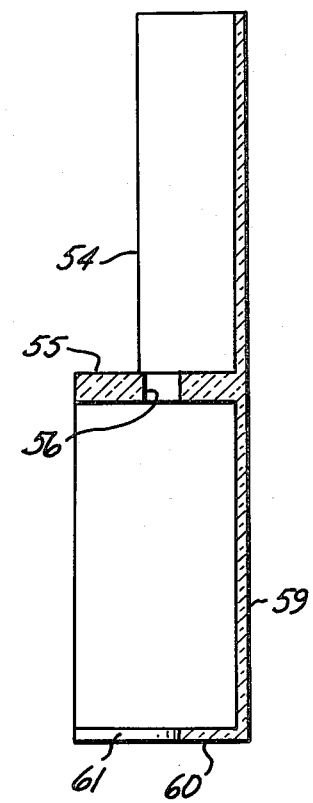
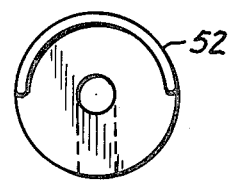
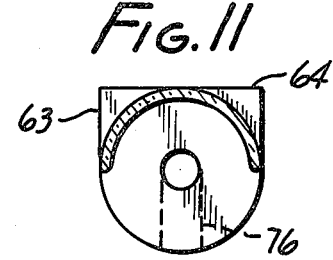
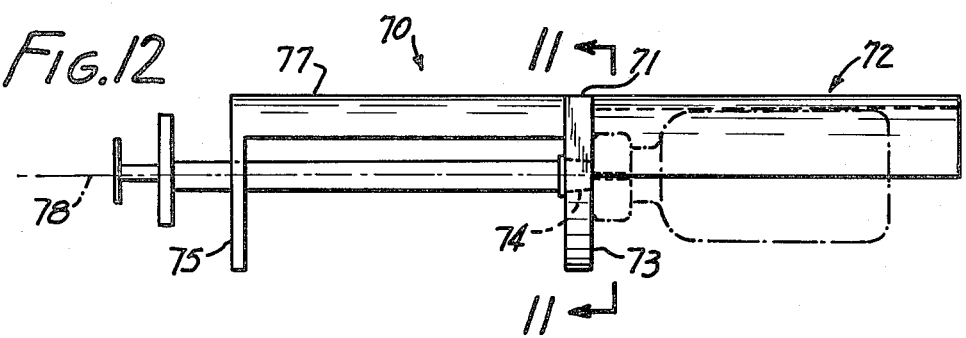

HOLDER FOR A SYRINGE AND AN AMPOULE

This application is a continuation of Ser. No. 376,009, filed May 7, 1982, now abandoned.

FIELD OF THE INVENTION

This invention relates to transferring of fluid from an ampoule to a syringe, and in particular to a holder for holding the ampoule and syringe to facilitate the transfer.

BACKGROUND OF THE INVENTION

Especially for the self administration of medicines from an ampoule by means of a syringe, this transfer must often be accomplished by persons who are ill and in relatively poor general condition with poor eyesight or tremors. A well-known example is diabetes where insulin, sometimes two types of insulin, must be transferred from an ampoule to a syringe in accurately measured amounts. One of the unfortunate consequences of diabetes is deterioration of the eyesight, and also frequently a person having diabetes is relatively aged and unsteady. The need to hold the ampoule, insert the needle into the ampoule and then withdraw the plunger of a syringe an accurate distance requires not only physical steadiness but also the ability to read the numbers on the syringe. This causes difficulties to the person requiring the medication, and often requires them to ask for assistance in filling the syringe which embarrasses, distresses, and delays them.

It is an object of this invention to provide a holder which frees the person from the requirement of holding the ampoule or holding the syringe individually.

Another object is to enable the needle automatically and accurately to be inserted into the ampoule, and if desired to provide magnifying means which will make the numbers on the syringe more readable even to a person with deteriorated eyesight.

BRIEF DESCRIPTION OF THE INVENTION

This invention comprises a holder for a syringe and an ampoule to facilitate the transfer of liquid from the ampoule to the syringe. It includes a unitary body with a trough-like section to receive the ampoule. A first wall member on the body is adjacent to the trough-like section. There is an aperture through the wall member to receive and support a portion of the syringe with its needle projecting into the trough-like section where it will puncture the ampoule. The body further includes a rest member spaced from the wall member, the rest member having an aperture to receive and support the syringe. At least a portion of the boundary of each of the apertures serves to align the syringe so that its needle is directed accurately toward an ampoule which rests in the trough-like section.

According to a preferred but optional feature of the invention, the body may also include a magnifier extending parallel to the axis of the syringe to magnify the numbers on the syringe and increase their readability.

The above and other features of this invention will be fully understood from the following detailed description and the accompanying drawings, in which:

BRIEF DESCRIPTION OF THE DRAWINGS

FIG. 1 is a top view of the presently preferred embodiment of the invention;

FIGS. 2 and 3 are right hand and bottom views of FIG. 1, respectively;

FIG. 4 is a view similar to FIG. 1 showing the syringe and ampoule in place;

FIGS. 5 and 6 are cross-sections taken at lines 5—5 and 6—6 in FIGS. 2 and 3, respectively;

FIG. 7 is a vignette taken at line 7—7 in FIG. 4;

FIG. 8 is a top view of another embodiment of the invention;

FIG. 9 is a right hand view of FIG. 8;

FIG. 10 is a cross-section taken at line 10—10 in FIG. 8;

FIG. 11 is a cross-section taken at line 11—11 in FIG. 12; and

FIG. 12 is a side view of another embodiment of the invention.

DETAILED DESCRIPTION OF THE INVENTION

The presently preferred embodiment of a holder 20 according to the invention is shown in FIG. 1. It includes a body 21 which has a trough-like section 22 formed by an embracing wall 23. End 24 of trough-like section 22 is open so than an ampoule can be inserted therein. Preferably, as best shown in FIG. 6, the wall extends for more than 180° around the axis 25 of the trough-like section. However, it need not extend for more than 180° nor need the interior of the embracing wall necessarily be part of a cylinder. Persons skilled in the art can readily design body structures which are slotted or otherwise modified so as to support an ampoule, but the illustrated embodiment is at once simple to manufacture because it is readily molded, and can be made of transparent material which will facilitate viewing the ampoule not only through the open slot 26 in the trough-like section but also through the wall itself if desired.

A wall member 30 is part of the body and placed adjacent to the trough-like section. It includes an aperture 31 on axis 25. The purpose of this axis is to permit admission of a portion of the syringe, as will later be seen. In this case the aperture is a hole. As will later be seen in some embodiments, it can be a slot instead.

A rest member 35 comprises a wall with an aperture 36, in this case a slot.

Bridging the distance between the wall member and the rest member is a portion of the body which may be modified to constitute an optical magnifier 40 that extends parallel to axis 25, and is so proportioned, disposed and arranged as to magnify the numbers on a syringe as will later be seen. The body then will have structure members extending between the wall member and the rest member in which case the magnifier can be made of optical glass or some preferred different optical material. However, the device shown can readily be constructed of molded, transparent material having a suitable index of refraction, for example, many acrylic plastics which are readily selected for their moldability and optical properties.

The function of this holder is best shown in FIG. 4, where an ampoule 41 is shown in the trough-like section with its head 42 adjacent to, and perhaps bearing against wall member 30. Before it was placed in the trough-like section, the syringe 43 will have been put in place by thrusting its hub 44 into aperture 31 of wall member 30 where it makes a close fit with at least part of the boundary of the aperture. Then barrel 45 of the syringe is pressed down in aperture 36 of the rest member, where it is held in a proper alignment. At least part of the boundary of aperture 36 will also support and align the syringe so that it is axially oriented. Then, with the needle properly projecting into the trough-like section, the ampoule is simply pressed down the trough so that its head is pierced by the syringe. Then the plunger is withdrawn, and if the magnifier is provided as in this embodiment it is, the enlarged numbers 46 can more easily be read through the magnifier.

The embodiment of FIG. 8 illustrates that the magnifier is optional and when it is not being used, a somewhat simpler construction can be provided, in this embodiment a holder 50 comprises a body 51, a trough-like section 52 extending along an axis 53. In this embodiment, its embracing wall 54 extends only 180° or less showing that an embracing of more than 180° periphery is optional, although it could instead be used.

A wall member 55 is provided with an aperture 56, again as a hole, to receive a syringe 57 and align the needle 58 in the trough-like section. Structure 59 leads to a rest member 60 which has an aperture 61 to form a slot that receives the barrel 62 of the syringe. The advantage of this embodiment is that the ampoule and the syringe can be manipulated from the same side. As best shown in FIG. 11, aperture 56 in the wall member could instead be made as a slot. Furthermore, protrusions 63, 64 can be provided to project from the body so that the device can be set down and will not roll away. Its function is the same as that of the embodiment of FIG. 1.

FIG. 12 shows another holder 70 with a body 71 having a trough-like section 72, a wall member 73 with an aperture 74, a rest member 75 with an aperture 76, and a magnifier 77. In this embodiment the magnifier and the wall member are on the same side of axis 78 of the device. Then the syringe and ampoule can be loaded from the same side, but the device will have to be turned over for observing the numbers. It might be more convenient for the wall of the trough-like section to be made transparent so the ampoule can also be observed. Alternatively it can be slotted for viewability.

In summary, it may be noted that the various features such as providing the aperture and wall member as either a slot or as a hole are optionally selectable so long as a portion of its boundary serves to align the syringe in the holder. The syringe is preferably snugly held in the apertures. The term "unitary" is used to denote one-piece article, with no part movable relative to any other part. The magnifier, for example, forms an integral part of the body.

This invention thereby provides a convenient holder for an ampoule and a syringe which optionally enables the numbers to be magnified, and which in any event makes the manipulation of the two items very much more convenient for the user.

This invention is not to be limited by the embodiments shown in the drawings and described in the description which are given by way of example and not of limitation, but only in accordance with the scope of the appended claims.

I claim:

1. A holder for a syringe and an ampoule of the type having a central puncturable portion, to facilitate the transfer of liquid from the ampoule to the syringe, comprising: a body having a trough-like section slidably to receive and support said ampoule, a wall member on said body adjacent to said trough-like section, there being an aperture through said wall member to receive and support a portion of said syringe, with its needle projecting into said trough-like section in alignment with said puncturable portion, whereby to puncture said puncturable portion when said ampoule is slid so its puncturable portion moves toward and upon said needle; a rest member spaced from said wall member, said rest member having an aperture to receive and support said syringe so as to limit its travel toward said trough-like section, at least a portion of the boundary of each of said apertures serving to align said syringe so that its needle is directed accurately toward said puncturable portion; and an optical magnifier between said rest member and said wall member, so disposed and arranged as to magnify the volume markings on a syringe supported in said two apertures, said trough-like section, wall member, rest member, and optical magnifier being formed as a unitary, one-piece said body, the length of said trough-like section being sufficient to enable the ampoule to be slid so its puncturable portion fully clears or fully engages the needle while being supported in said section.

2. A holder according to claim 1 in which said trough-like section is at least partially defined by a wall which extends more than 180° degrees around an ampoule that rests in said trough-like section.

3. A holder according to claim 1 in which the aperture in said wall member is a hole through said wall member.

4. A holder according to claim 1 in which the aperture in said wall member is a slot extending to an outer edge thereof.

5. A holder according to claim 1 in which the aperture in said rest member is a slot extending to an outer edge thereof.

6. A holder according to claim 1 in which said magnifier is a semi-cylindrical magnifier.

7. A holder according to claim 1 in which said trough-like section and said magnifier are on opposite sides of an axis through a syringe supported in said apertures, whereby the ampoule is directly viewable by the user, and the syringe is viewable through the magnifier.

8. A holder according to claim 1 in which said trough-like section and said magnifier are on the same side of an axis extending through a syringe supported in said apertures.

9. A holder according to claim 8 in which at least a portion of said trough-like section is transparent, whereby the ampoule can be viewed through it.

10. A holder according to claim 1 in which said trough-like section is open at its end farthest removed from said wall member.

11. A holder according to claim 10 in which said trough-like section is at least partially defined by a wall which extends more than 180° degrees around an ampoule which rests in said trough-like section.

12. A holder according to claim 1 in which a protrusion extends from said body to prevent the body from rolling on a surface.

* * * * *